(12) United States Patent
Hampel et al.

(10) Patent No.: US 7,983,384 B2
(45) Date of Patent: Jul. 19, 2011

(54) X-RAY COMPUTED TOMOGRAPHY ARRANGEMENT

(75) Inventors: Uwe Hampel, Dresden (DE); Frank Fischer, Dresden (DE)

(73) Assignee: Helmholtz-Zentrum Dresden-Rossendorf e.V., Dresden (DE)

( * ) Notice: Subject to any disclaimer, the term of this patent is extended or adjusted under 35 U.S.C. 154(b) by 0 days.

(21) Appl. No.: 12/527,928

(22) PCT Filed: Feb. 12, 2008

(86) PCT No.: PCT/DE2008/000268
§ 371 (c)(1), (2), (4) Date: Aug. 20, 2009

(87) PCT Pub. No.: WO2008/101470
PCT Pub. Date: Aug. 28, 2008

(65) Prior Publication Data
US 2010/0034341 A1    Feb. 11, 2010

(30) Foreign Application Priority Data

Feb. 20, 2007 (DE) .......................... 10 2007 008 349

(51) Int. Cl.
*G01N 23/083* (2006.01)
(52) U.S. Cl. ............................................................. 378/10
(58) Field of Classification Search ................ 378/10
See application file for complete search history.

(56) References Cited

U.S. PATENT DOCUMENTS

| | | | | |
|---|---|---|---|---|
| 4,199,684 A * | 4/1980 | Leunbach et al. | ............ | 378/137 |
| 4,274,005 A * | 6/1981 | Yamamura et al. | ................ | 378/9 |
| 4,287,425 A | 9/1981 | Elliott, Jr. | | |
| 4,352,021 A * | 9/1982 | Boyd et al. | ....................... | 378/12 |
| 5,191,600 A * | 3/1993 | Vincent et al. | ................... | 378/10 |
| 5,305,363 A * | 4/1994 | Burke et al. | ........................ | 378/4 |
| 6,731,716 B2 * | 5/2004 | Mihara et al. | ...................... | 378/9 |
| 7,142,629 B2 * | 11/2006 | Edie et al. | ........................... | 378/9 |
| 7,203,269 B2 * | 4/2007 | Huber et al. | .................... | 378/10 |
| 7,233,644 B1 * | 6/2007 | Bendahan et al. | .............. | 378/57 |
| 7,295,651 B2 * | 11/2007 | Delgado et al. | .................. | 378/92 |
| 7,428,297 B2 * | 9/2008 | Eilbert | ............................ | 378/134 |
| 2004/0017888 A1 | 1/2004 | Seppi et al. | | |

FOREIGN PATENT DOCUMENTS

| | | |
|---|---|---|
| DE | 4015180 A1 | 11/1991 |
| GB | 1602494 A | 11/1981 |

* cited by examiner

*Primary Examiner* — Edward J Glick
*Assistant Examiner* — Thomas R Artman
(74) *Attorney, Agent, or Firm* — Laurence A. Greenberg; Werner H. Stemer; Ralph E. Locher

(57) ABSTRACT

The aim of the invention is to produce an x-ray computed tomography arrangement in which there is no axial offset between the path of the focal spot and the x-ray detector arc. Said aim is achieved by: —arranging the x-ray detector arc and the target around the examination cross-section within a radiation plane such that the x-ray focal spots generated by the deflected electron beam of the electron beam generator lie within an axial plane, the radiation plane, along with the active detector elements; —disposing the x-ray detector arc behind the target in a radial direction such that each imaginary x-ray extending from a focal spot position on the target to a detector element of the x-ray detector arc penetrates the target, which lies in front of the point of incidence on the x-ray detector arc in the direction of radiation, in the area in which the target and the x-ray detector arc angularly overlap; —producing the target from a target member which is preferably made of a material that has a low atomic number and great heat storage capacity or thermal conductance; —applying an electron-decelerating material layer, preferably made of a refractory material that has a high atomic number, to the side of the target member which faces the electron beam.

12 Claims, 2 Drawing Sheets

X-RAY COMPUTED TOMOGRAPHY ARRANGEMENT

BACKGROUND OF THE INVENTION

Field of the Invention

The invention relates to an X-ray computed tomography arrangement.

Electron beam X-ray tomography has been used in medical diagnosis for a number of years now, in particular for imaging the beating heart. In the process, an electron beam guided in a vacuum chamber is guided over a metal target of part circular design by means of an electromagnetic deflection system, as a result of which an X-ray focus which can be moved quickly is generated. An X-ray detector of circular or part circular design, arranged slightly offset in the axial direction with respect to the target, detects the X-rays transmitted through the body. The material distribution in the radiated slice plane can be calculated from the measured data by applying tomographic image reconstruction methods.

It follows from tomographic image reconstruction theory that the integral attenuation value of each beam running through the slice area to be reconstructed must be measured and included in the calculation of the reconstruction for the error-free reconstruction of an object slice from its line integral projections. In the case of a CT scanner with a fixed arc-shaped X-ray target and fixed X-ray detector arc, the consequence of this is that the required detector angle and the required target angle together have to result in at least 360° plus the fan angle, that is to say in more than 360°. This in turn means that part of the X-ray detector and the target have to lie within a common solid angle region when seen from the system axis. This problem is solved in a structural manner such that X-ray target and X-ray detector are arranged with a slight axial offset with respect to one another, that is to say in different axial planes. Such arrangements for electron beam X-ray tomography are described, for example, in the documents U.S. Pat. No. 4,352,021 and U.S. Pat. No. 5,504,791.

The problem of the axial offset and the imaging error caused thereby was detected at an early stage, and different methods for solving it were attempted. In general, the error can be minimized by keeping the axial offset structurally as small as possible. For medical electron beam tomography scanners with a relatively large aspect ratio between the organ to be imaged (heart) and the diameter of the target or of the X-ray detector arc, a certain amount of optimization can thus be attained. For electron beam tomography scanners with small target and X-ray detector arc diameters, this variant has structural limits.

US 2003/0161434 describes an arrangement in which target and X-ray detector are designed in a helical form and are arranged offset with respect to one another around the examination object so that, for almost all focal positions, respectively part of the detector helix lies in the same axial plane on the other side of the examination object. This arrangement can implement so-called spiral CT recording. A disadvantage of this arrangement is the complex form of target and X-ray detector which causes high costs.

DE 10 356 601 describes an arrangement in which target and X-ray detector are arranged within a plane without axial offset. A disadvantage of this arrangement is that the angular region of the radiation is smaller than what is required for acquiring a complete tomographic data record. Hence, slice images calculated from measured data of this measurement arrangement are corrupted to a certain extent.

BRIEF SUMMARY OF THE INVENTION

The object of the present invention is to specify an X-ray computed tomography arrangement which does not require an axial offset between the focal path and X-ray detector arc.

The object is achieved by the features of claim 1. Refinements of the invention are listed in the dependent claims.

An X-ray target, through which radiation can pass and which is composed of a mechanically stable target body composed of materials with a low atomic number and a high heat storage capacity or thermal conductivity, is utilized, as well as a thin layer of a refractory metal which is applied to this target body, has a high atomic number and is used for decelerating the electron beam and hence for generating the X-rays.

The main advantage of the invented X-ray computed tomography arrangement with a target through which radiation can pass consists of target and X-ray detector arcs being able to be arranged completely within one axial plane, and hence complete tomographic data recording being possible precisely within this axial plane. This achieves the highest possible image quality and axial spatial resolution. The arrangement can be applied in particular to electron beam tomography scanners or other CT scanners with a fixed source-detector combination. It is particularly advantageous for relatively small examination geometries, for example in small-animal scanners, since in such arrangements even a small axial offset leads to significant image blurring and image errors as a result of the small source-detector spacing.

The implementation of X-ray computed tomography (CT) which is without offset in the axial direction is ensured for a CT scanner with a fixed source-detector combination. With respect to CT scanners currently used in practice, the arrangement is suitable in particular for electron beam computed tomography scanners in which a moveable X-ray focus is generated by means of an electromagnetically deflected electron beam. However, additionally, the arrangement is in principle suitable for every type of CT scanner with fixed X-ray detector and X-ray target where the target would partly cover the X-ray detector in the case of a recording to be implemented entirely within one axial plane. By way of example, it is also suitable for a CT scanner with a multiplicity of electron beam generators which are arranged annularly around the examination cross section and which focus the electron beam onto either a single arc-shaped target or a multiplicity of targets. The invention affords the possibility of acquiring complete data records within a slice plane of an object in the sense of tomographic image reconstruction theory and, in the process, imaging the object cross section with the maximum possible axial spatial resolution determined only by the focal geometry and the axial extent of the detector elements.

In the following text, the invention will be explained in more detail on the basis of exemplary embodiments.

In the associated drawing,

DESCRIPTION OF THE INVENTION

Figure 1:
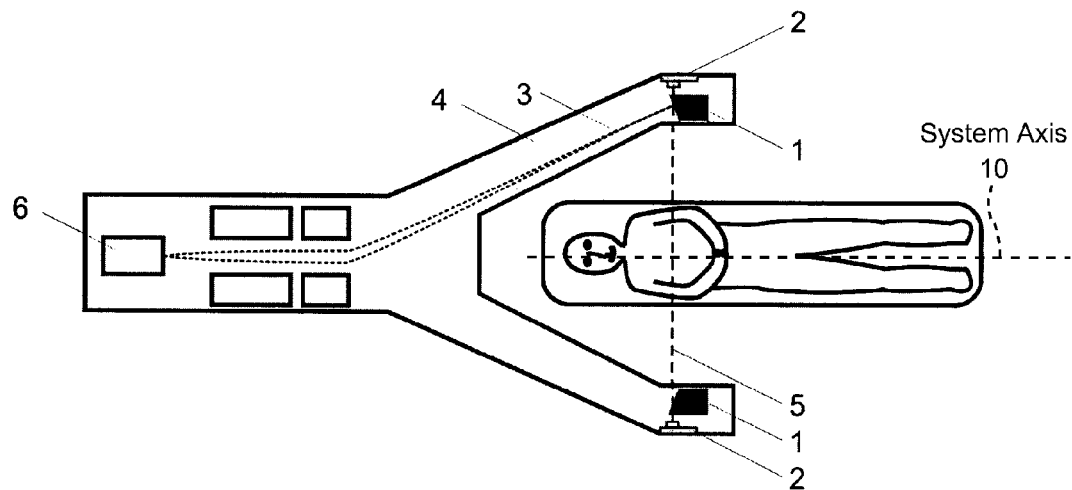
FIG. 1 shows the overall arrangement with an internal X-ray detector arc.
Figure 2:
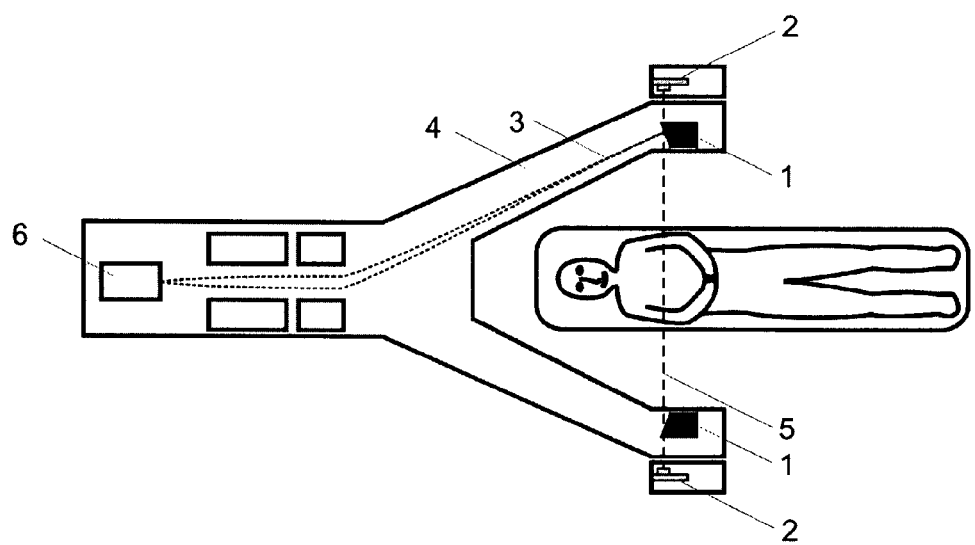
FIG. 2 shows the overall arrangement with an external X-ray detector arc.

FIGS. 1 and 2 show two exemplary embodiments of the arrangement using the example of axial offset-free electron beam X-ray tomography. In both cases, the arrangement consists of a target (1) of part circular design and an X-ray detector arc (2) arranged outside of the target (1) and comprising individual detectors arranged next to one another. The electron beam (3) is guided to the target (1) through the vacuum chamber (4) and generates an X-ray focus on the target surface. Said focus is moved along a circular or ellipsoidal path on the target (1) by means of beam deflection by a deflection coil system. The X-ray detector arc (2) is arranged such that the detector elements and the focal path lie in one axial plane, the radiation plane (5), that is orthogonal to the system axis (10 of FIG. 1). In the exemplary embodiment of FIG. 1, the X-ray detector arc (2) is arranged within the vacuum chamber (4), and in the exemplary embodiment of FIG. 2, said arc is arranged outside of the vacuum chamber (4).

Figure 3:
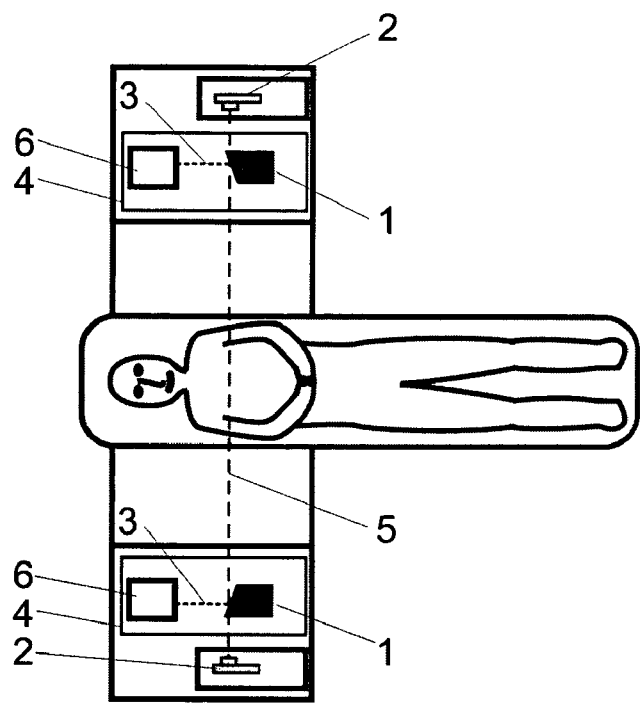
FIG. 3 shows a variant of the arrangement in accordance with FIG. 1.

FIG. 3 shows an alternative variant of an axial offset-free X-ray CT arrangement with a plurality of electronically switchable electron beam generators (6) which are arranged around the examination cross section and guide an electron beam (3) onto a common target (1) of part circular design in temporal succession and thereby enable a sequential recording of X-ray projections of the object cross section from different angles. With respect to this exemplary embodiment, it should be noted that the arrangement, in addition to the variant with a continuous vacuum chamber (4) with a solid target (1) demonstrated in the exemplary embodiment, can likewise be designed as a multiplicity of individual X-ray sources with in each case one electron beam generator (6) and a target (1) within respectively one vacuum chamber (4), or as a multiplicity of X-ray sources with respectively a group of electron beam generators (6) and a target (1) or a multiplicity of targets (1) in respectively one vacuum chamber (4).

Figure 4:
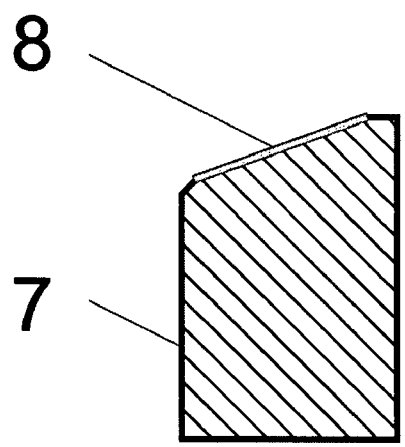
FIG. 4 shows a slice through the target.

In accordance with FIG. 4, the target (1) consists of a target body (7), preferably composed of a material with a low atomic number and a high heat storage capacity or thermal conductivity, and a material layer (8) applied to this target body (7) for decelerating electrons, preferably composed of a refractory material with a high atomic number. By way of example, graphite, diamond or titanium are possible materials for the target body (7); molybdenum or tungsten are possible for the electron-decelerating material layer (8). The thickness of the electron-decelerating material layer (8) is selected in accordance with the maximum penetration depth of the electrons into the target material.

Figure 5:
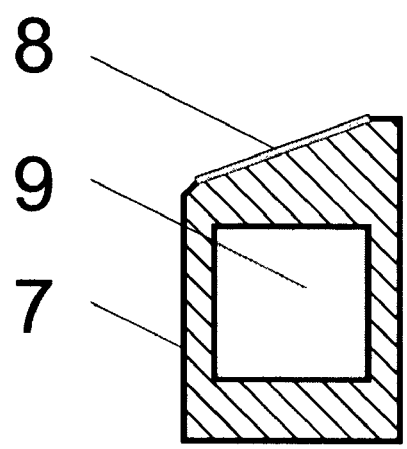
FIG. 5 shows a slice through a target that can be cooled.

In accordance with FIG. 5, a coolant channel (9) is provided within the target body (7) for a cooling liquid to flow through the target body (7).

LIST OF REFERENCE SYMBOLS

1 Target
2 X-ray detector arc
3 Electron beam
4 Vacuum chamber
5 Radiation plane
6 Electron beam generator
7 Target body
8 Material layer
9 Coolant channel
10 System axis

The invention claimed is:

1. An X-ray computed tomography arrangement, comprising:

an X-ray detector arc of part or full circular design made of individual detectors arranged next to one another;

an electron beam generator configured to generate, focus and deflect an electron beam within a vacuum chamber;

at least one target arranged within the vacuum chamber for decelerating the electron beam and for generating X-rays;

the X-ray detector arc and the at least one target being arranged around an examination cross section so that an X-ray foci generated on a surface of the target by an electron beam generated by the electron beam generator and guided by beam deflection, and the active detector elements lie within an axial plane relative to a system axis;

the X-ray detector arc being arranged behind the target in the radial direction relative to the system axis, so that every X-ray beam extending from an X-ray foci on the target to a detector element of the X-ray detector arc passes through the target lying in front, relative to the system axis, of an impact point on the X-ray detector arc in a region of angular overlap of target and X-ray detector arc;

the target is composed of a target body which is preferably formed by a material with a low atomic number and a high heat storage capacity or thermal conductivity; and an electron-decelerating material layer, preferably composed of a refractory material with a high atomic number, is applied to the side of the target body facing the electron beam.

2. The arrangement as claimed in claim 1, wherein the X-ray detector arc is arranged outside of the vacuum chamber, the vacuum chamber being composed of a thin-walled material which ensures low attenuation of the X-rays.

3. The arrangement as claimed in claim 1, further including a coolant channel within the target body, said coolant channel being configured to permit fluid to flow therethrough.

4. The arrangement as claimed in claim 1, wherein said electron beam generator includes a multiplicity of electronically switchable electron beam generators, which can be briefly switched on one after the other during a tomographic scan, arranged within the vacuum chamber.

5. The arrangement as claimed in claim 1, wherein said electron beam generator and said at least one target are disposed together in said vacuum chamber to form an X-ray emitter, said arrangement including a multiplicity of X-ray emitters, composed in each case of an electron beam generator and a target arranged in a separate vacuum chamber around the examination cross section, which X-ray emitters are configured to be switched on one after the other during a tomography scan.

6. The arrangement as claimed in claim 1, wherein the target has a stepped design in an axial direction relative to the system axis and wherein one or more X-ray detector arcs lying one behind the other in the axial direction relative to the system axis are arranged around the target to image the examination object three-dimensionally without a translation movement by generating different focal paths in different axial planes by a corresponding deflection movement of the electron beam.

7. An X-ray computed tomography arrangement, comprising:
- an X-ray detector arc of part or full circular design made of individual detectors arranged next to one another;
- an electron beam generator configured to generate, focus and deflect an electron beam within a vacuum chamber;
- at least one target through which radiation can pass being arranged within the vacuum chamber for decelerating the electron beam and for generating X-rays;
- the X-ray detector arc and the at least one target being arranged around the examination cross section so that an X-ray foci generated on a surface of the target by an electron beam generated by the electron beam generator and guided by beam deflection and the active detector elements lie within an axial plane relative to a system axis;
- the X-ray detector arc being arranged behind the target in the radial direction relative to the system axis, so that every X-ray beam extending from an X-ray foci on the target to a detector element of the X-ray detector arc passes through the target lying in front, relative to the system axis, of an impact point on the X-ray detector arc in a region of angular overlap of target and X-ray detector arc;
- the target is composed of a target body which is preferably formed by a material with a low atomic number and a high heat storage capacity or thermal conductivity; and
- an electron-decelerating material layer, preferably composed of a refractory material with a high atomic number, is applied to the side of the target body facing the electron beam.

8. The arrangement as claimed in claim 7, wherein the X-ray detector arc is arranged outside of the vacuum chamber, the vacuum chamber being composed of a thin-walled material which ensures low attenuation of the X-rays.

9. The arrangement as claimed in claim 7, further including a coolant channel within the target body, said coolant channel being configured to permit fluid to flow therethrough.

10. The arrangement as claimed in claim 7, wherein said electron beam generator includes a multiplicity of electronically switchable electron beam generators, which can be briefly switched on one after the other during a tomographic scan, arranged within the vacuum chamber.

11. The arrangement as claimed in claim 7, wherein said electron beam generator and said at least one target are disposed together in said vacuum chamber to form an X-ray emitter, said arrangement including a multiplicity of X-ray emitters, composed in each case of an electron beam generator and a target arranged in a separate vacuum chamber around the examination cross section, which X-ray emitters are configured to be switched on one after the other during a tomography scan.

12. The arrangement as claimed in claim 7, wherein the target has a stepped design in an axial direction relative to the system axis and wherein one or more X-ray detector arcs lying one behind the other in the axial direction relative to the system axis are arranged around the target to image the examination object three-dimensionally without a translation movement by generating different focal paths in different axial planes by a corresponding deflection movement of the electron beam.

* * * * *